(12) United States Patent
Schwing et al.

(10) Patent No.: US 8,363,918 B2
(45) Date of Patent: Jan. 29, 2013

(54) METHOD AND SYSTEM FOR ANATOMIC LANDMARK DETECTION USING CONSTRAINED MARGINAL SPACE LEARNING AND GEOMETRIC INFERENCE

(75) Inventors: Alexander Schwing, Zurich (CH); Yefeng Zheng, Dayton, NJ (US); Martin Harder, Nürnberg (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 477 days.

(21) Appl. No.: 12/604,495

(22) Filed: Oct. 23, 2009

(65) Prior Publication Data
US 2010/0119137 A1   May 13, 2010

Related U.S. Application Data

(60) Provisional application No. 61/113,705, filed on Nov. 12, 2008.

(51) Int. Cl.
*A61B 6/03* (2006.01)
(52) U.S. Cl. ...................................................... 382/131
(58) Field of Classification Search ................... 382/131
See application file for complete search history.

(56) References Cited

U.S. PATENT DOCUMENTS

| | | |
|---|---|---|
| 2008/0085050 A1 | 4/2008 | Barbu et al. |
| 2008/0101676 A1 | 5/2008 | Zheng et al. |
| 2008/0211812 A1 | 9/2008 | Barbu et al. |
| 2009/0080745 A1 | 3/2009 | Zheng et al. |
| 2009/0087066 A1 | 4/2009 | Odry et al. |

OTHER PUBLICATIONS

Zheng et al., Four-Chambered Heart Modeling and Automatic Segmentation for 3D Cardiac CT Volumes, Mar. 11, 2008, SPIE vol. 6914, pp. 16-1 to 16-12.*
Zheng et al., Constrained Marginal Space Learning for Efficient Anatomical Structure detection in Medical Images, Jun. 2009, IEEE Conference on Computer Vision and Pattern Recognition, CVPR 2009, pp. 194-201.*
Carneiro et al., Detection and Measurement of Fetal Anatomies from Ultrasound Images using a Constrained Probabilistic Boosting Tree, Published Jul. 29, 2008, IEEE, vol. 27, No. 9, pp. 1342-1355.*

* cited by examiner

*Primary Examiner* — Toan Ton
*Assistant Examiner* — John Corbett

(57) ABSTRACT

A method and apparatus for detecting multiple anatomical landmarks in a 3D volume. A first anatomical landmark is detected in a 3D volume using marginal space learning (MSL). Locations of remaining anatomical landmarks are estimated in the 3D volume based on the detected first anatomical landmark using a learned geometric model relating the anatomical landmarks. Each of the remaining anatomical landmarks is then detected using MSL in a portion of the 3D volume constrained based on the estimated location of each remaining landmark. This method can be used to detect the anatomical landmarks of the crista galli (CG), tip of the occipital bone (OB), anterior of the corpus callosum (ACC), and posterior of the corpus callosum (PCC) in a brain magnetic resonance imaging (MRI) volume.

23 Claims, 5 Drawing Sheets

METHOD AND SYSTEM FOR ANATOMIC LANDMARK DETECTION USING CONSTRAINED MARGINAL SPACE LEARNING AND GEOMETRIC INFERENCE

This application claims the benefit of U.S. Provisional Application No. 61/113,705, filed Nov. 12, 2008, the disclosure of which is herein incorporated by reference.

BACKGROUND OF THE INVENTION

The present invention relates to 3D object detection in images, and more particularly, to automated detection of 3D anatomical structures in medical images using marginal space learning.

Efficiently localizing anatomical structures (e.g., heart, liver, kidney, etc.) in medical images is often a prerequisite for further diagnostic image processing procedures, such as segmentation, measuring, and classification. Detecting and segmenting human anatomic structures in 3D medical image volumes (e.g., CT, MRI, etc.) is a challenging problem, which is typically more difficult than detecting anatomic structures in 2D images.

Previously, marginal space learning (MSL) has been proposed for efficient and automatic 3D object localization based on learning of discriminative classifiers. The full parameter space for 3D object localization has nine dimensions: three for position ($P_x$, $P_y$, and $P_z$), three for orientation (represented with Euler angles, $\psi$, $\phi$, and $\theta$), and three for anisotropic scaling ($S_x$, $S_y$, and $S_z$). In MSL, in order to efficiently localize an object, parameter estimation is performed in a series of marginal spaces with increasing dimensionality. In particular, the object detection is split into three steps: object position estimation, position-orientation estimation, and similarity transformation estimation. Each step results in a relatively small number of candidates, which are used in the following step. Accordingly, instead of uniformly searching the original nine-dimensional parameter space, low-dimensional marginal spaces are uniformly searched in MSL. MSL has been successfully applied to many 3D anatomical detection problems in medical imaging, such as ileocecal valves, polyps, and livers in abdominal CT, brain tissues and heart chambers in ultrasound images, and heart chambers in MRI.

MSL can reduce the number of testing hypotheses by approximately six orders of magnitude as compared with uniformly searching the nine-dimensional parameter space. However, in many cases MSL tests more testing hypotheses than necessary for accurate object detection. Accordingly, it is desirable to further increase the efficiency of anatomical object detection using MSL.

BRIEF SUMMARY OF THE INVENTION

The present invention provides efficient detection of 3D anatomical landmarks in medical images using constrained marginal space learning (MSL) and geometric inference. Embodiments of the present invention can be used to constrain the search space for landmark detection by exploiting geometric constraints among object pose parameters (i.e., position, orientation, and scale) of multiple 3D anatomical landmarks.

In one embodiment of the present invention, a first landmark of a plurality of anatomical landmarks is detected in an image using marginal space learning (MSL). Locations of remaining landmarks of the plurality of anatomical landmarks are estimated in the image based on the detected first landmark using a learned geometric model relating the plurality of anatomical landmarks. Each of the remaining landmarks is then detected using MSL in a portion of the image constrained based on the estimated location of each of the remaining landmarks.

These and other advantages of the invention will be apparent to those of ordinary skill in the art by reference to the following detailed description and the accompanying drawings.

DETAILED DESCRIPTION

Figure 1:
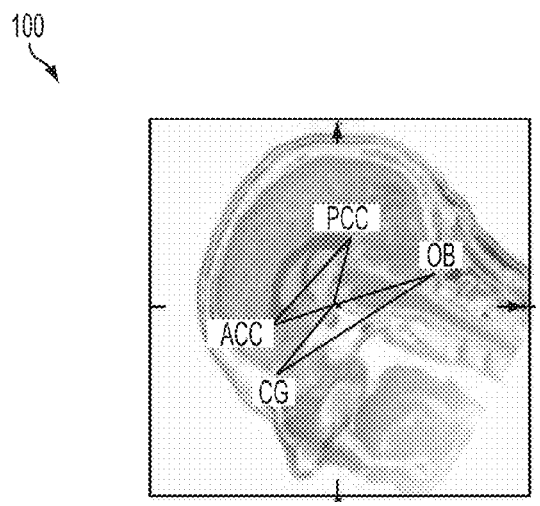
FIG. 1 illustrates a slice of an MR brain volume showing the four anatomic landmarks.

The present invention is directed to a method for detecting anatomical landmarks in medical images, such as computed tomography (CT), magnetic resonance imaging (MRI), ultrasound, etc. Embodiments of the present invention are described herein to give a visual understanding of the anatomical landmark detection method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

According to an embodiment of the present invention, an anatomical structure is detected in a 3D medical image using constrained marginal space learning (MSL). MSL is a technique for efficiently detecting or localizing a 3D object in an image using learned discriminative classifiers. The full parameter space for 3D object localization has nine dimensions: three for position ($P_x$, $P_y$, and $P_z$), three for orientation (represented with Euler angles, $\psi$, $\phi$, and $\theta$), and three for anisotropic scaling ($S_x$, $S_y$, and $S_z$). In order to efficiently localize an object using MSL, parameter estimation is performed in a series of marginal spaces with increasing dimensionality. In particular, the object detection is split into three steps: object position estimation, position-orientation estimation, and similarity transformation estimation. Each of these steps uses a separately trained classifier. For example, a classifier for each detection step can be trained based on training data using the concept of the probabilistic boosting tree (PBT). The present invention is not limited to a PBT and other classifiers can be similarly applied.

MSL has been successfully applied to many 3D anatomical structures detection problems in medical imaging (e.g., ileocecal valve, polyps, and livers in abdominal CT images, brain tissues and heart chambers in ultrasound images, and heart chambers in MRI images). Depending on the application scenario, it is possible to reduce the search range within each marginal space.

In some applications, MSL can be used to detect multiple anatomic landmarks in a volume. For example, in techniques for automatically setting the scan prescription in MR brain scanning, a localizer image of the brain is acquired. Various landmarks, such as the crista galli, tip of the occipital bone, anterior of the corpus collosum, and posterior of the corpus collosum, are detected in the localizer image and the scan prescription is set based on the detected landmarks. Each of these landmarks may be detected using separate MSL searches. Embodiments of the present invention, exploit geometric relationships between anatomic landmarks in a volume to constrain the search space of multiple MSL searches.

Embodiments of the present invention are directed to detecting a number $N_t$ of anatomic landmarks in a medical image. Embodiments of the present invention are directed to detecting anatomic landmarks in 3D medical imaging volumes, and are described herein using the example of detecting multiple landmarks in a brain MRI volume. However, it is to be understood that the present invention is not limited to any particular anatomic location, number of landmarks, or medical imaging modality. Further, the present invention is not limited to 3D volumes, and can be similarly applied to 2D images as well.

According to an exemplary embodiment, four ($N_l$=4) anatomic landmarks $y_j$, $j \in \{1, \ldots, N_l\}$ are detected in a brain MRI volume. FIG. 1 illustrates a cross-section 100 of an MR brain volume showing the four anatomic landmarks. As illustrated in FIG. 1, the four anatomic landmarks are the crista galli (CG), the tip of the occipital bone (OB), the anterior of the corpus callosum (ACC), and the posterior of the corpus callosum (PCC).

Geometric models relating the multiple parameters can be trained based on annotated training data. For all available training volumes t, a $3 \cdot N_t$ dimensional ground truth vector $$[y_{1,t}^T, \ldots, y_{N_l,t}^T]^T \in \mathfrak{R}^{3 \cdot N_t}$$

of annotations is needed. Multiple geometric models $i \in \{1, \ldots N_d\}$ can be constructed. For each training volume t, the geometric model includes a position $t_{i,t} \in \mathfrak{R}^3$, orientation, $R_{i,t} \in SO(3)$ represented, for example, in quaternion representation, and scale $S_{i,t} = \text{diag}\{s_{i,t,x}, s_{i,t,y}, s_{i,t,z}\} \in \mathfrak{R}^{3 \times 3}$. Using these model parameters, the annotations can be converted in the local coordinate system using:

$$\bar{y}_{i,j,t} = S_{i,t}^{-1} R_{i,t}^T (y_{j,t} - t_{i,t}). \quad (1)$$

The local geometric models are obtained from the mean shape, i.e. by applying:

$$\bar{y}_{i,j} = \frac{1}{N_t} \sum_{t=1}^{N_t} \bar{y}_{i,j,t}. \quad (2)$$

The learned mean geometric model resulting from Equation (2) is used in the landmark detection method described below.

Figure 2:
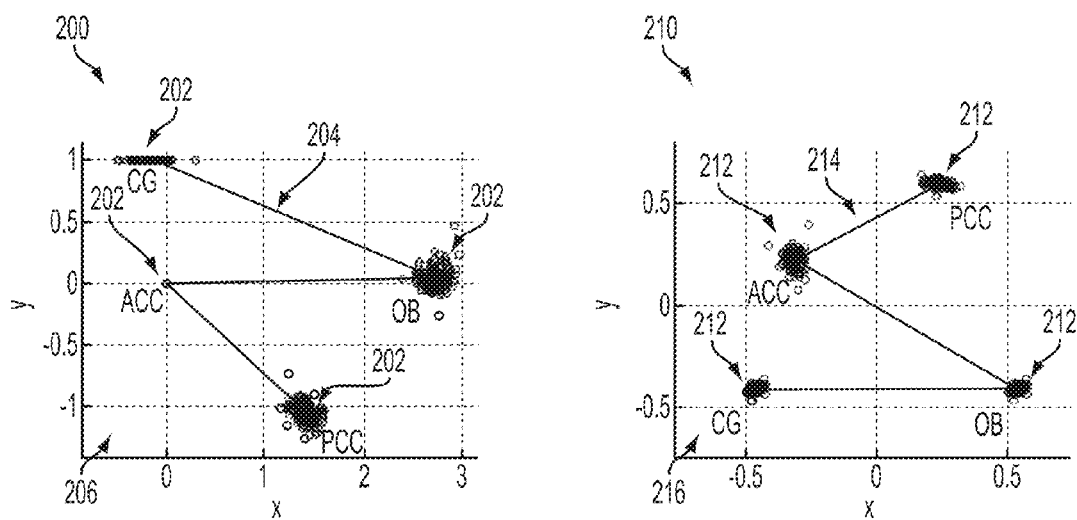
FIG. 2 illustrates exemplary geometric models learned from training data.

FIG. 2 illustrates exemplary geometric models 200 and 210 learned from training data. As illustrated in FIG. 2, in model 200, annotations 202 for the CG, OB, and PCC from multiple training volumes are converted to a local coordinate system 206, and the mean shape 204 of the geometric model is calculated. In model 210, annotations 212 for the CG, OB, ACC, and PCC from multiple training volumes are converted to a local coordinate system 216, and the mean shape 214 of the geometric model is calculated.

MSL can be applied to detect multiple parameters by training a detector for each geometric model. Thus, $N_d$ detectors are obtained. According to an embodiment of the present invention, instead of searching the entire volume using all of the detectors, the detection of landmarks can be approached successively using a first detected location and geometric inference.

Figure 3:
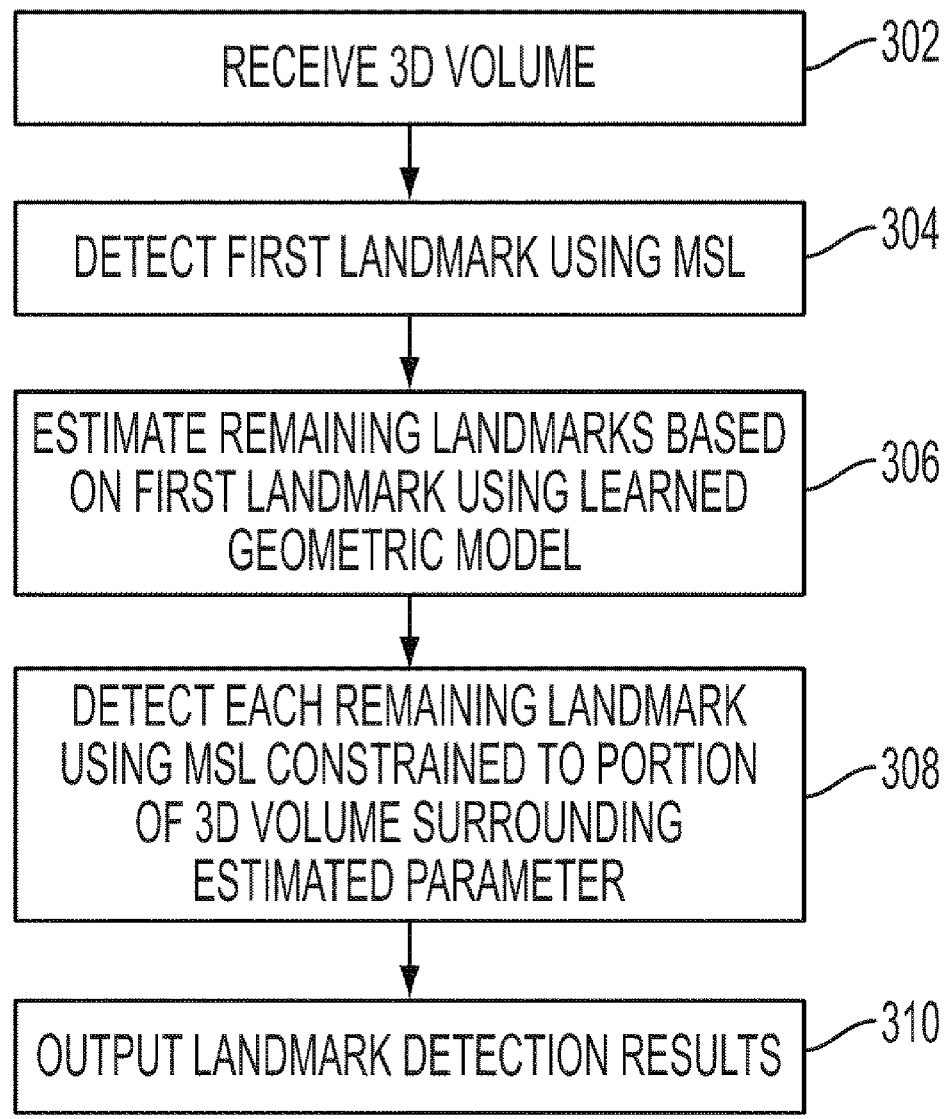
FIG. 3 illustrates a method of detecting multiple anatomic landmarks in a 3D volume according to an embodiment of the present invention.

FIG. 3 illustrates a method of detecting multiple anatomic landmarks in a 3D volume according to an embodiment of the present invention. FIG. 3 is described by referring to the example of detecting the CG, OB, ACC, and PCC in a brain MRI volume, but the method is not limited thereto, and can be used for detection of any number of landmarks in any anatomical location and any medical imaging modality.

At step 302, a 3D volume is received. In one embodiment, the 3D volume can be a brain MRI volume. However, the present invention is not limited thereto, and the 3D volume can be a medical image resulting from any type of imaging modality. The 3D volume can be received directly from an image acquisition device, such as an MR scanner. It is also possible that the 3D volume can be received by loading a 3D volume stored, for example, on a memory or storage of a computer system or some other computer readable storage medium.

Figure 4:
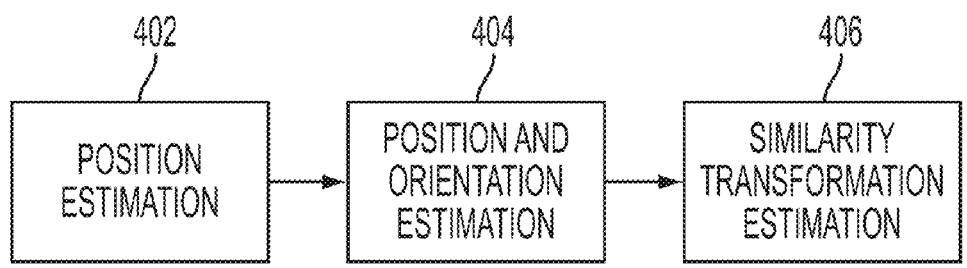
FIG. 4 illustrates stages of marginal space learning (MSL)

At step 304, a first anatomical landmark is detected in the 3D volume using MSL. In particular first landmark detector that has been trained based on training data is used to scan the entire 3D volume to detect the first landmark. The first landmark detector utilizes three classifiers corresponding to the three stages of MSL. FIG. 4 illustrates the stages of MSL. As illustrated in FIG. 4, the first landmark is detected in the 3D volume using a position estimation stage 402, a position-orientation stage 404, and a full similarity transformation stage 406. A classifier is trained for each of the MSL stages 402, 404, and 406 based on training data using a PBT. The position classifier detects candidates for the position of the first landmark in the 3D volume. Position-orientation hypotheses are generated from detected position candidates. The position-orientation classifier detects position-orientation candidates from the position-orientation hypotheses. Similarity transformation hypotheses are generated from the position-orientation candidates. The similarity transformation classifier than detects similarity transformation candidates from the similarity transformation hypotheses. The similarity transformation (position, orientation, and scale) for the first anatomic landmark can be determined by selecting the best similarity transformation candidate or by aggregating a certain number of best similarity transformation candidates. In the example of anatomical landmark in a brain MRI volume, any one of the CG, OB, ACC, and PCC can be detected as the first landmark using MSL.

Returning to FIG. 3, at step 306, the locations of the remaining anatomic landmarks are estimated in the 3D volume based on the detected first anatomic landmarks using a learned geometric model. As described above, geometric models relating the multiple anatomic landmarks, such as those shown in FIG. 2, are trained based on annotated training data. The detection of the first anatomic landmark results in a nine parameter similarity transformation. This similarity transformation is used to transform the mean shape of the learned geometric model obtained by Equations (1) and (2) in order to infer the locations of all of the remaining anatomical landmarks based on the first anatomic landmark.

Figure 5:
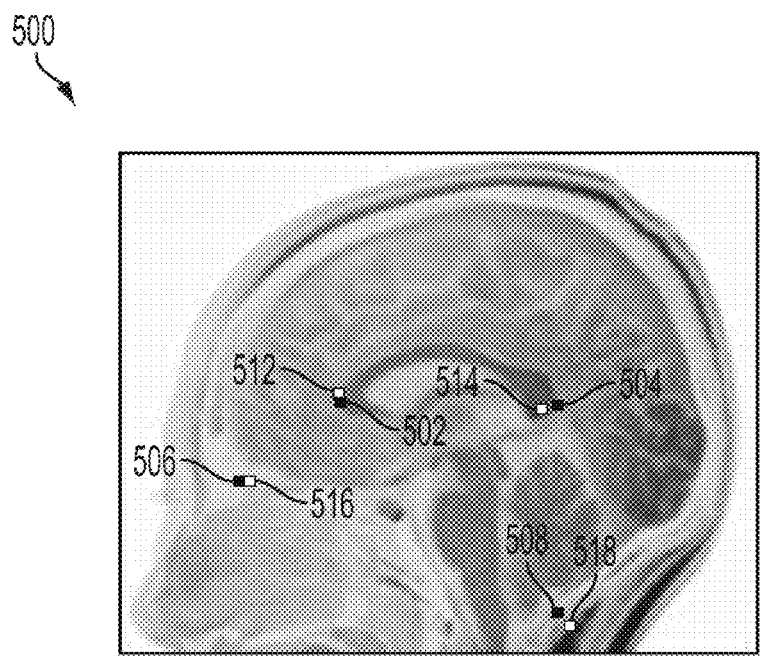
FIG. 5 illustrates results of estimating anatomic landmarks in a brain MRI volume based on a first detected anatomic landmark using a learned geometric model.

FIG. 5 illustrates results of estimating anatomic landmarks in a brain MRI volume based on a first detected anatomic landmark using a learned geometric model. As illustrated in FIG. 5, image 500 is a cross-section of a brain MRI volume showing annotated ground truth locations for the ACC 502, PCC 504, CG 506, and OB 508. Image 500 also shows estimated locations of the ACC 512, PCC 524, CG 516, and OB 508 resulting from detecting one or the landmarks using MSL and inferring the remaining landmarks based on the detected landmark using a geometric model.

Returning to FIG. 3, at step 308, each of the remaining anatomical landmarks (i.e., the landmarks other than the first landmark) are detected using MSL constrained to a portion of the 3D volume surrounding the estimated location of the each anatomical landmark. The trained MSL-based detector for each landmark is used to detect the landmark in a constrained parameter space surrounding the estimated location of the landmark. For example, the position classifier of each landmark detector may only scan voxels within a certain distance of the estimated location of the landmark as potential candidates for the position of the landmark. MSL detection can then continues as describe above or stop after position detection. The constrained MSL detection of each landmark refines the position of each landmark estimated using the geometric model. It is to be understood that although the first anatomical landmark is not required to be further refined using constrained MSL, according to a possible implementation, the first anatomical landmark can also be refined using MSL detection constrained based on the previously detected location of the first anatomical landmark.

Once the locations of the anatomical landmarks are refined using the constrained MSL detection, it is possible to further constrain the results to a valid output based on known properties of the anatomical landmarks being detected. For example, in the example of detecting the anatomical landmarks of the CG, OB, ACC, and PCC in a brain MRI volume, the landmarks can be constrained to a plane (i.e., the midsagittal plane). In this case, the landmarks can be constrained by solving the least square minimization problem:

$$\min_{n,p} \sum_{j=1}^{N_l} ((y_j - p)^T n)^2 \text{ s.t. } \|n\|_2^2 = 1, \quad (3)$$

and projecting the detected results to the plane using, for example, a well-known Gram-Schimdt optimization. In Equation (3), $y_j$ denotes the detected anatomical landmarks, p denotes the position of the plane, and n denotes the plane normal.

At step 310, the anatomical landmark detection results are output. The detection results can be output by displaying the detection results on a display of a computer system. The anatomical landmark detection results can also be output by storing the detection results, for example, on a memory or storage of a computer system or on a computer readable storage medium. It is possible to use the anatomical landmark detection results in subsequent medical imaging techniques. For example, detected anatomical landmarks in a localizer brain MRI volume can be used in MRI scan planning to determine an alignment of an MR scanner for a high resolution scan.

Figure 6:
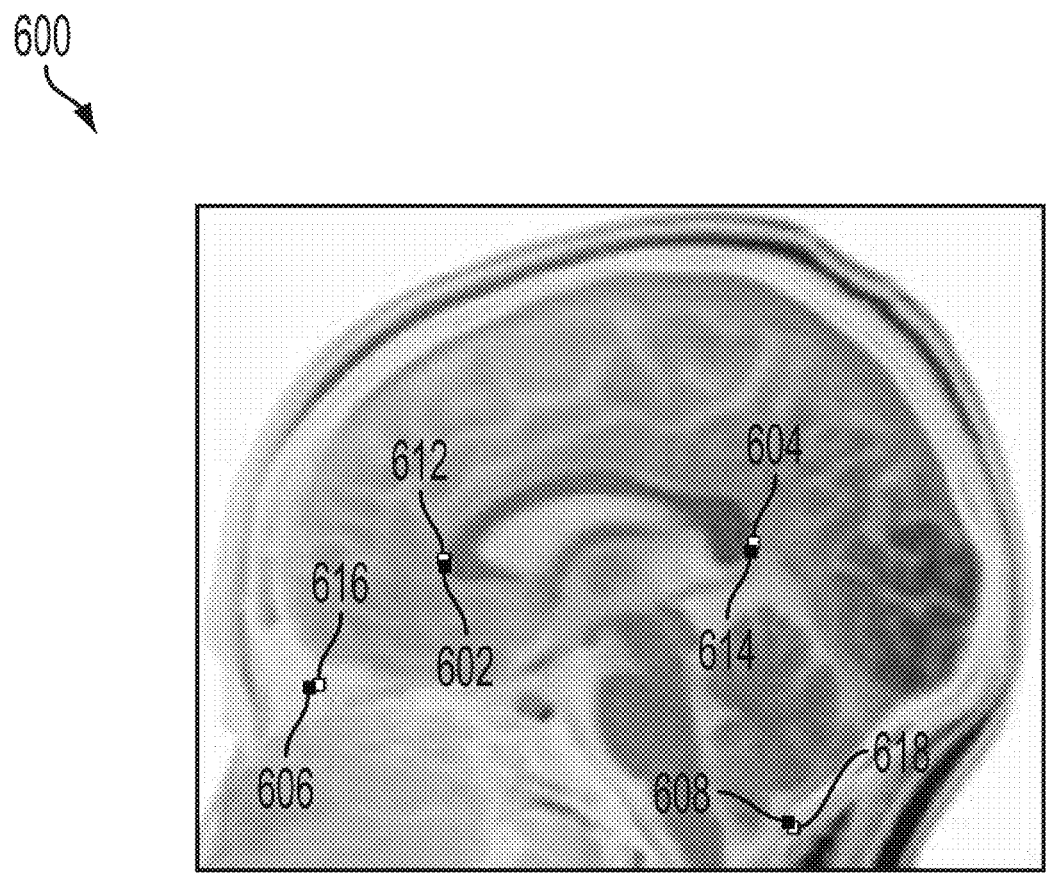
FIG. 6 illustrates exemplary detection results of anatomical structures in a brain MRI volume.

FIG. 6 illustrates exemplary detection results of anatomical structures in a brain MRI volume. As illustrated in FIG. 6, image 600 is a cross-section of a brain MRI volume showing annotated ground truth locations for the ACC 602, PCC 604, CG 606, and OB 608 as well as the final detected locations for the ACC 612, PCC 614, CG 616, and OB 618. The final detected anatomical landmark locations 612, 614, 616, and 618 are detected using MSL constrained based on the estimated anatomical landmark locations 512, 514, 516, and 518 shown in FIG. 5.

Figure 7:
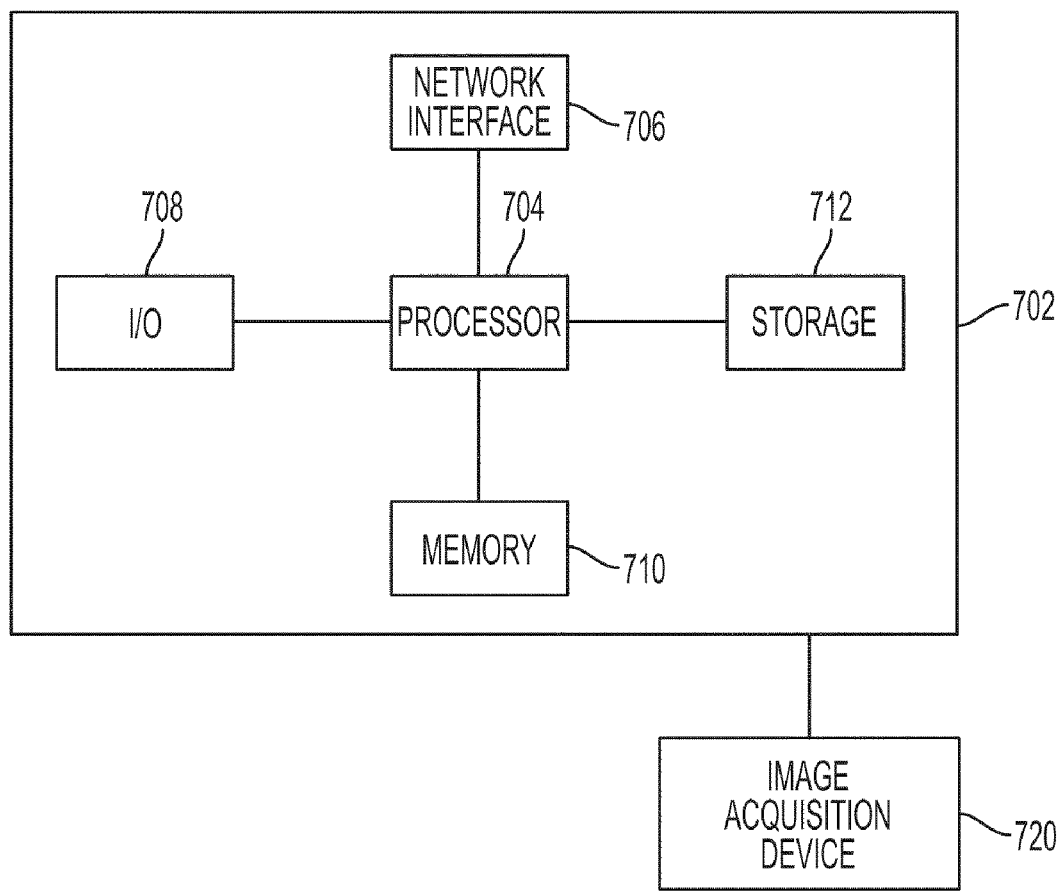
FIG. 7 is a high level block diagram of a computer capable of implementing the present invention.

The above-described methods for anatomical landmark detection may be implemented on a computer using well-known computer processors, memory units, storage devices, computer software, and other components. A high level block diagram of such a computer is illustrated in FIG. 7. Computer 702 contains a processor 704 which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIG. 3 may be defined by the computer program instructions stored in the memory 710 and/or storage 712 and controlled by the processor 704 executing the computer program instructions. An image acquisition device 720, such as an MRI scanning device, can be connected to the computer 702 to input the 3D images (volumes) to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.) One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for detecting a plurality of anatomical landmarks in an image comprising:
   detecting a first landmark of the plurality of anatomical landmarks in the image using marginal space learning (MSL);
   estimating locations of remaining landmarks of the plurality of anatomical landmarks in the image based on the detected first landmark using a learned geometric model relating the plurality of anatomical landmarks; and
   detecting each of said remaining landmarks using MSL in a portion of the image constrained based on the estimated location of each of said remaining landmarks.

2. The method of claim 1, wherein said step of detecting a first landmark of the plurality of anatomical landmarks in the image using MSL comprises:

detecting position candidates in the image for the first landmark using a trained position classifier;
generating position-orientation hypotheses from said position candidates;
detecting position-orientation candidates from said position-orientation hypotheses using a trained position-orientation classifier;
generating similarity transformation hypotheses from said position-orientation candidates; and
detecting at least one similarity transformation candidate from said similarity transformation hypotheses using a trained similarity transformation classifier.

3. The method of claim 2, wherein the position classifier, the position-orientation classifier, and the similarity transformation classifier are each trained based on training data using a probabilistic boosting tree (PBT).

4. The method of claim 1, wherein the learned geometric model is a mean shape relating the plurality of anatomical landmarks trained based on training data.

5. The method of claim 1, wherein said step of estimating locations of remaining landmarks of the plurality of anatomical landmarks in the image on the detected first landmark using a learned geometric model relating the plurality of anatomical landmarks comprises:
transforming a mean shape of the learned geometric model based on a similarity transformation of the detected first landmark.

6. The method of claim 1, wherein said step of detecting each of said remaining landmarks using MSL in a portion of the image constrained based on the estimated location of each of said remaining landmarks comprises, for each of said remaining landmarks:
detecting position candidates in a portion of the image within a certain distance of the estimated location of the landmark using a trained position classifier;
generating position-orientation hypotheses from said position candidates;
detecting position-orientation candidates from said position-orientation hypotheses using a trained position-orientation classifier;
generating similarity transformation hypotheses from said position-orientation candidates; and
detecting at least one similarity transformation candidate from said similarity transformation hypotheses using a trained similarity transformation classifier.

7. The method of claim 1, wherein the image is a 3D volume.

8. The method of claim 1, wherein the image comprises a brain MRI volume and the plurality of anatomical landmarks comprises a crista galli (CG), a tip of the occipital bone (OB), an anterior of the corpus callosum (ACC), and a posterior of the corpus callosum (PCC).

9. The method of claim 8, further comprising:
constraining detected locations for each of CG, OB, ACC, and PCC to be on a plane.

10. An apparatus for detecting a plurality of anatomical landmarks in an image comprising:
means for detecting a first landmark of the plurality of anatomical landmarks in the image using marginal space learning (MSL);
means for estimating locations of remaining landmarks of the plurality of anatomical landmarks in the image based on the detected first landmark using a learned geometric model relating the plurality of anatomical landmarks; and
means for detecting each of said remaining landmarks using MSL in a portion of the image constrained based on the estimated location of each of said remaining landmarks.

11. The apparatus of claim 10, wherein said means for detecting a first landmark of the plurality of anatomical landmarks in the image using MSL comprises:
means for detecting position candidates in the image for the first landmark using a trained position classifier;
means for generating position-orientation hypotheses from said position candidates;
means for detecting position-orientation candidates from said position-orientation hypotheses using a trained position-orientation classifier;
means for generating similarity transformation hypotheses from said position-orientation candidates; and
means for detecting at least one similarity transformation candidate from said similarity transformation hypotheses using a trained similarity transformation classifier.

12. The apparatus of claim 10, wherein the learned geometric model is a mean shape relating the plurality of anatomical landmarks trained based on training data.

13. The apparatus of claim 10, wherein said means for estimating locations of remaining landmarks of the plurality of anatomical landmarks in the image based on the detected first landmark using a learned geometric model relating the plurality of anatomical landmarks comprises:
means for transforming a mean shape of the learned geometric model based on a similarity transformation of the detected first landmark.

14. The apparatus of claim 10, wherein said means for detecting each of said remaining landmarks using MSL in a portion of the image constrained based on the estimated location of each of said remaining landmarks comprises:
means for detecting position candidates in a portion of the image within a certain distance of an estimated location of a landmark using a trained position classifier;
means for generating position-orientation hypotheses from said position candidates;
means for detecting position-orientation candidates from said position-orientation hypotheses using a trained position-orientation classifier;
means for generating similarity transformation hypotheses from said position-orientation candidates; and
means for detecting at least one similarity transformation candidate from said similarity transformation hypotheses using a trained similarity transformation classifier.

15. The apparatus of claim 10, wherein the image is a 3D volume.

16. The apparatus of claim 10, wherein the image comprises a brain MRI volume and the plurality of anatomical landmarks comprises a crista galli (CG), a tip of the occipital bone (OB), an anterior of the corpus callosum (ACC), and a posterior of the corpus callosum (PCC).

17. A computer readable medium encoded with computer executable instructions for detecting a plurality of anatomical landmarks in an image, the computer executable instructions defining steps comprising:
detecting a first landmark of the plurality of anatomical landmarks in the image using marginal space learning (MSL);
estimating locations of remaining landmarks of the plurality of anatomical landmarks in the image based on the detected first landmark using a learned geometric model relating the plurality of anatomical landmarks; and detecting each of said remaining landmarks using MSL in a portion of the image constrained based on the estimated location of each of said remaining landmarks.

18. The computer readable medium of claim 17, wherein the computer executable instructions defining the step of detecting a first landmark of the plurality of anatomical landmarks in the image using MSL comprise computer executable instructions defining the steps of:

detecting position candidates in the image for the first landmark using a trained position classifier;

generating position-orientation hypotheses from said position candidates;

detecting position-orientation candidates from said position-orientation hypotheses using a trained position-orientation classifier;

generating similarity transformation hypotheses from said position-orientation candidates; and detecting at least one similarity transformation candidate from said similarity transformation hypotheses using a trained similarity transformation classifier.

19. The computer readable medium of claim 17, wherein the learned geometric model is a mean shape relating the plurality of anatomical landmarks trained based on training data.

20. The computer readable medium of claim 17, wherein the computer executable instructions defining the step of estimating locations of remaining landmarks of the plurality of anatomical landmarks in the image based on the detected first landmark using a learned geometric model relating the plurality of anatomical landmarks comprise computer executable instructions defining the step of:

transforming a mean shape of the learned geometric model based on a similarity transformation of the detected first landmark.

21. The computer readable medium of claim 17, wherein the computer executable instructions defining the step of detecting each of said remaining landmarks using MSL in a portion of the image constrained based on the estimated location of each of said remaining landmarks comprise computer executable instructions defining the steps of, for each of said remaining landmarks:

detecting position candidates in a portion of the image within a certain distance of the estimated location of the landmark using a trained position classifier;

generating position-orientation hypotheses from said position candidates;

detecting position-orientation candidates from said position-orientation hypotheses using a trained position-orientation classifier;

generating similarity transformation hypotheses from said position-orientation candidates; and detecting at least one similarity transformation candidate from said similarity transformation hypotheses using a trained similarity transformation classifier.

22. The computer readable medium of claim 17, wherein the image is a 3D volume.

23. The computer readable medium of claim 17, wherein the image comprises a brain MRI volume and the plurality of anatomical landmarks comprises a crista galli (CG), a tip of the occipital bone (OB), an anterior of the corpus callosum (ACC), and a posterior of the corpus callosum (PCC).

\* \* \* \* \*